US010602922B2

(12) United States Patent
Bartozzi

(10) Patent No.: US 10,602,922 B2
(45) Date of Patent: Mar. 31, 2020

(54) INTUBATION DEVICE

(71) Applicant: Lennon Keith Bartozzi, Collierville, TN (US)

(72) Inventor: Lennon Keith Bartozzi, Collierville, TN (US)

(*) Notice: Subject to any disclaimer, the term of this patent is extended or adjusted under 35 U.S.C. 154(b) by 123 days.

(21) Appl. No.: 15/394,504

(22) Filed: Dec. 29, 2016

(65) Prior Publication Data

US 2017/0181614 A1 Jun. 29, 2017

Related U.S. Application Data

(60) Provisional application No. 62/272,251, filed on Dec. 29, 2015.

(51) Int. Cl.
*A61B 1/267* (2006.01)
*A61M 16/04* (2006.01)
*A61B 1/00* (2006.01)

(52) U.S. Cl.
CPC ........ *A61B 1/2673* (2013.01); *A61B 1/00071* (2013.01); *A61M 16/0488* (2013.01); *A61M 16/0495* (2014.02)

(58) Field of Classification Search
CPC .............................. A61B 1/267; A61B 1/2673
USPC ................................. 600/185, 190, 193–197
See application file for complete search history.

(56) References Cited

U.S. PATENT DOCUMENTS 2,127,215 A 8/1938 Gwathmey
3,716,047 A 2/1973 Moore et al.
5,092,314 A 3/1992 Zeitels
5,178,132 A * 1/1993 Mahefky ................ A61B 1/267 600/194
5,498,231 A * 3/1996 Franicevic ............. A61B 1/267 128/200.26
5,938,591 A * 8/1999 Minson .................. A61B 1/267 600/191
6,090,040 A 7/2000 Metro
6,991,604 B2 1/2006 Cantrell
7,153,260 B1 12/2006 Girgis
7,500,948 B2 3/2009 Cantrell
8,083,672 B2 * 12/2011 Minson .................. A61B 1/267 600/190
8,202,215 B2 6/2012 Xiao et al.
8,302,597 B2 * 11/2012 Beely ................ A61M 16/0493 128/200.26
8,444,556 B2 * 5/2013 Minson .................. A61B 1/267 600/190
8,464,710 B1 * 6/2013 Franckowiak .... A61M 16/0488 128/200.15

(Continued)

FOREIGN PATENT DOCUMENTS

| | | |
|---|---|---|
| JP | 2012-196300 | 10/2012 |
| KR | 10-2010-0131111 | 12/2010 |
| WO | 9428785 | 12/1994 |

*Primary Examiner* — Anu Ramana
(74) *Attorney, Agent, or Firm* — Baker Donelson

(57) ABSTRACT

A device used for oral intubation on a patient having a mouth and airway (or oropharynx) is disclosed. The device comprises a hard palate pivot support attached to a laryngoscope blade by a plurality of actuating arms, wherein the hard palate pivot support is used to push against the roof of a patient's mouth and consequently open a patient's airway in order to visualize the vocal chords. A method of use is further disclosed.

5 Claims, 15 Drawing Sheets

(56) References Cited

U.S. PATENT DOCUMENTS

| | | | |
|---|---|---|---|
| 2006/0074276 | A1 | 4/2006 | Cantrell |
| 2013/0109923 | A1 | 5/2013 | Trakas |

* cited by examiner

INTUBATION DEVICE

CROSS-REFERENCE TO RELATED APPLICATION(S)

The present application derives priority from U.S. Provisional Patent Application Ser. No. 62/272,251, filed Dec. 29, 2015, and which is incorporated herein by reference.

BACKGROUND OF THE INVENTION

Oral intubation is a procedure by which a tube is inserted through the mouth down into the trachea, the large airway from the mouth to the lungs. The tube is often inserted with the a laryngoscope, an instrument that permits the person inserting the tube to see the upper portion of the trachea, just below the vocal cords. During the procedure, the laryngoscope is used to hold the tongue to the side while the tube is inserted into the trachea. Critical to the procedure is that the head of the patient be positioned in the appropriate manner to allow for proper visualization. Additionally, pressure is typically applied to the thyroid cartilage (or Adam's apple) to allow better visualization of the trachea and to prevent possible aspiration.

Oral intubation is often a difficult medical procedure because the anatomy of some patients makes it difficult to view the patient's vocal chords, which is essential for successful intubation. Examples of patients where oral intubation is difficult include overweight patients, patients with an anterior placed trachea, patients with a short neck such as pediatric patients, and/or patients requiring intubation out in the field in an emergency situation. The existing methods of oral intubation involve prying forward on the patient's upper lip and teeth with the standard laryngoscope blade which often causes injury and, most importantly, results in an unsuccessful intubation or view of the patient's vocal chords. When the laryngoscope blade is tilted back into the upper lip and teeth, injury to the patient, such as broken teeth and lacerations to the interior of the mouth, may occur.

A device for oral intubation that may be easily used to provide successful oral intubation to difficult-to-intubate patients is needed. A device that uses a hard palate pivot support as a safe anchor point to push against the roof of a patient's mouth and consequently open the airway (or oropharynx) in order to visualize the vocal chords is needed.

SUMMARY OF THE INVENTION

A laryngoscope for use in pre-hospital and hospital situations is disclosed. The device is designed to increase the success rate of oral intubation of adult and pediatric patients. The device utilizes unique features that allow for one handed operation and use. The one-handed operation allows the healthcare worker performing the intubation to hold the device in one hand and free up the other hand for insertion of the endotracheal tube. The purpose of the device is to overcome obstacles that present themselves in any intubation situation. This device eliminates the requirement of physical arm strength by utilizing an anatomically friendly design and easy to use handle. The device allows for direct visualization of the vocal chords and will increase the success rate of intubations while decreasing the risk of injury to patients.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

Figure 6:
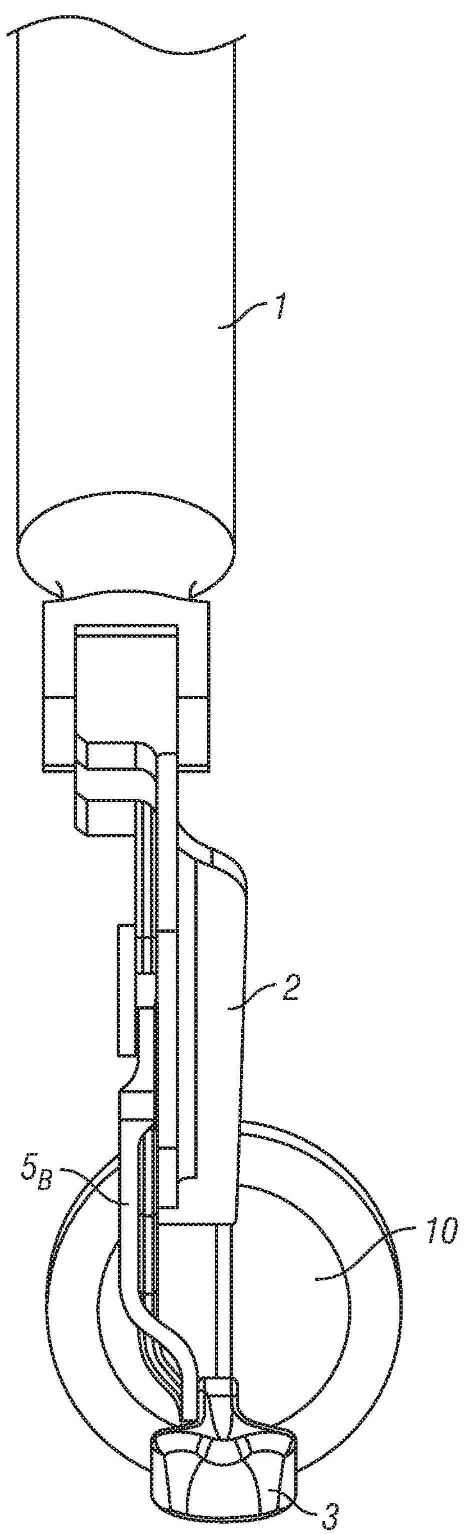
FIG. 6 is a top perspective view of the intubation device in use. Such depiction portrays a view of a perspective airway provided by the intubation device.
Figure 7:
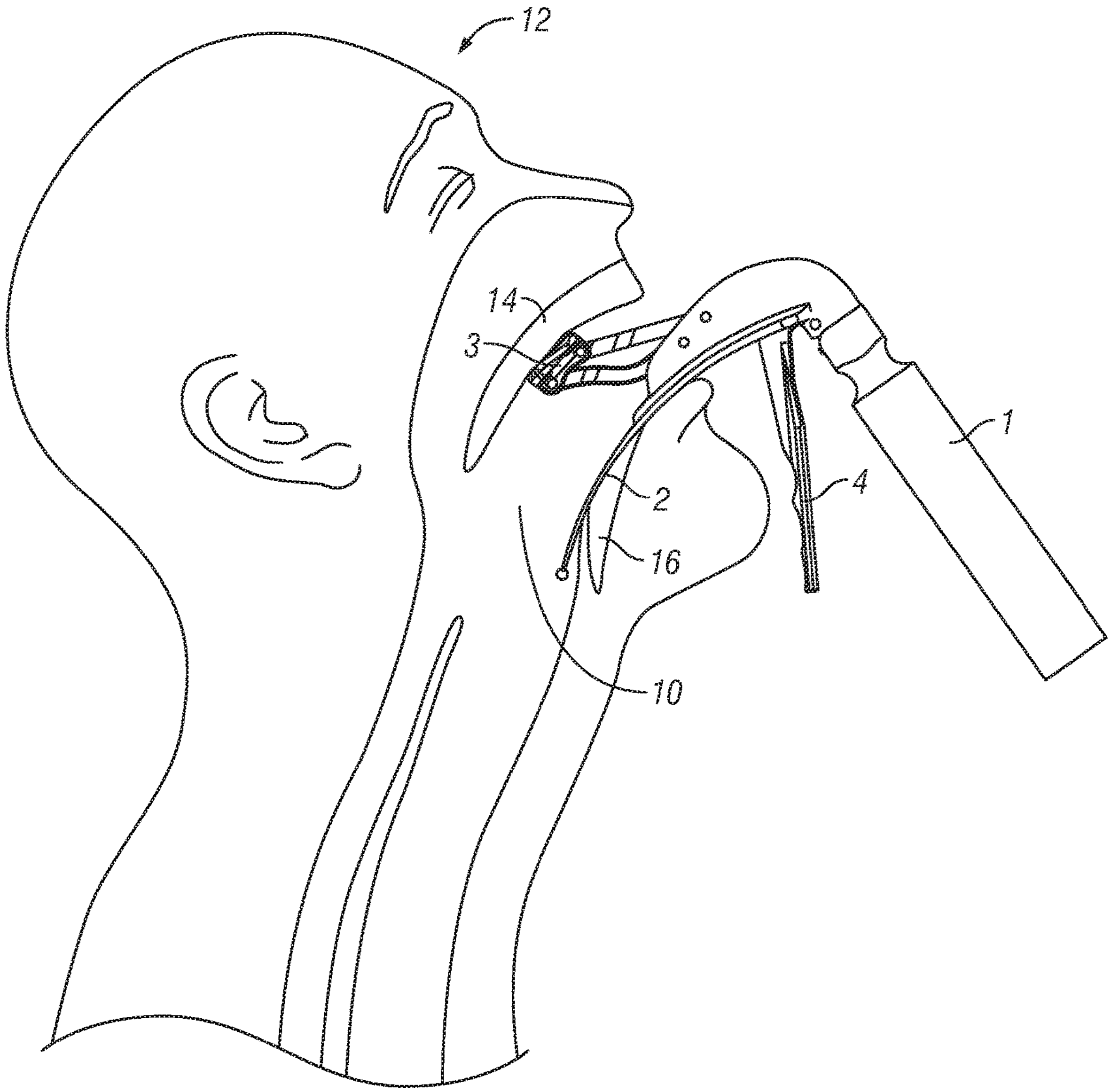
FIG. 7 is a side perspective view of the intubation device inserted into the mouth of a patient.
Figure 8:
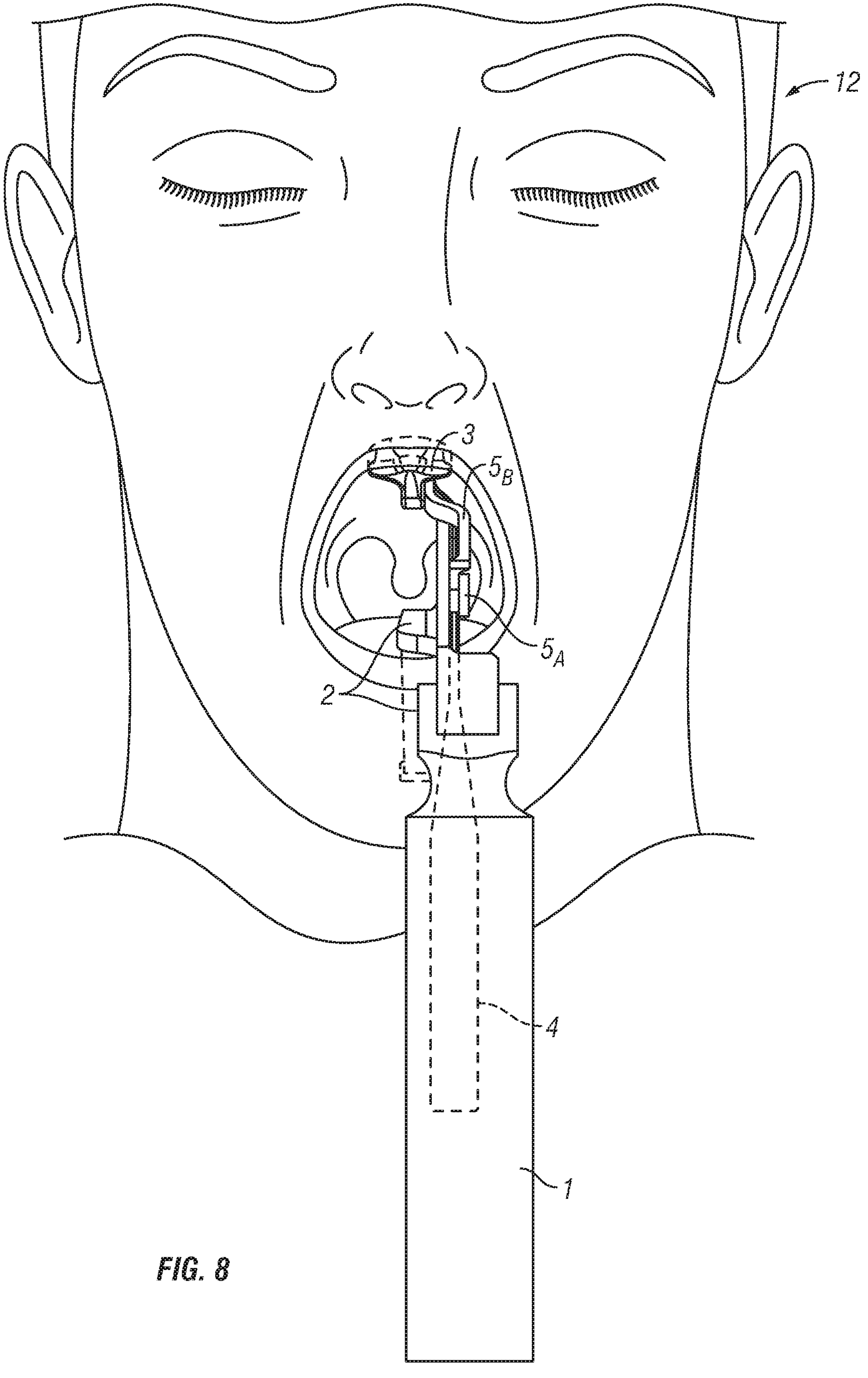
FIG. 8 is a front perspective view of the intubation device of FIG. 6.
Figure 9:
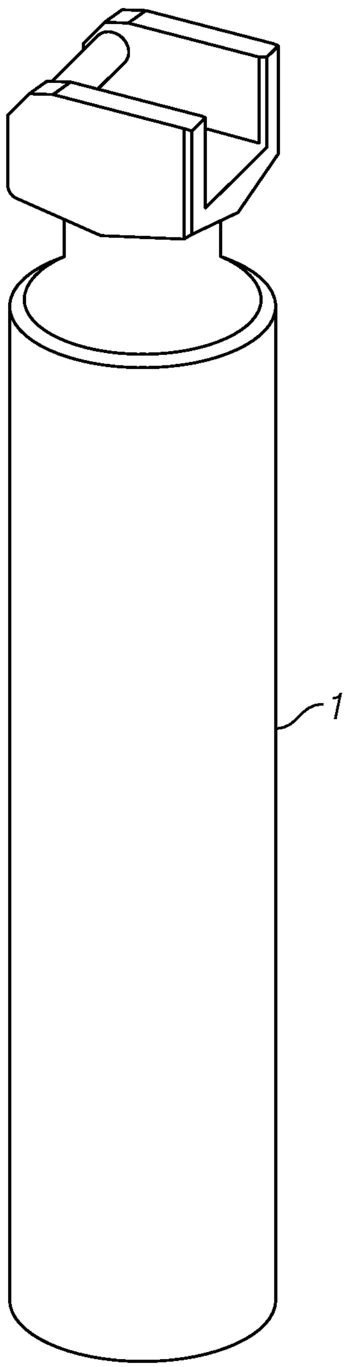
FIG. 9 is a perspective view of the handle of the intubation device of FIG. 1.
Figure 10:
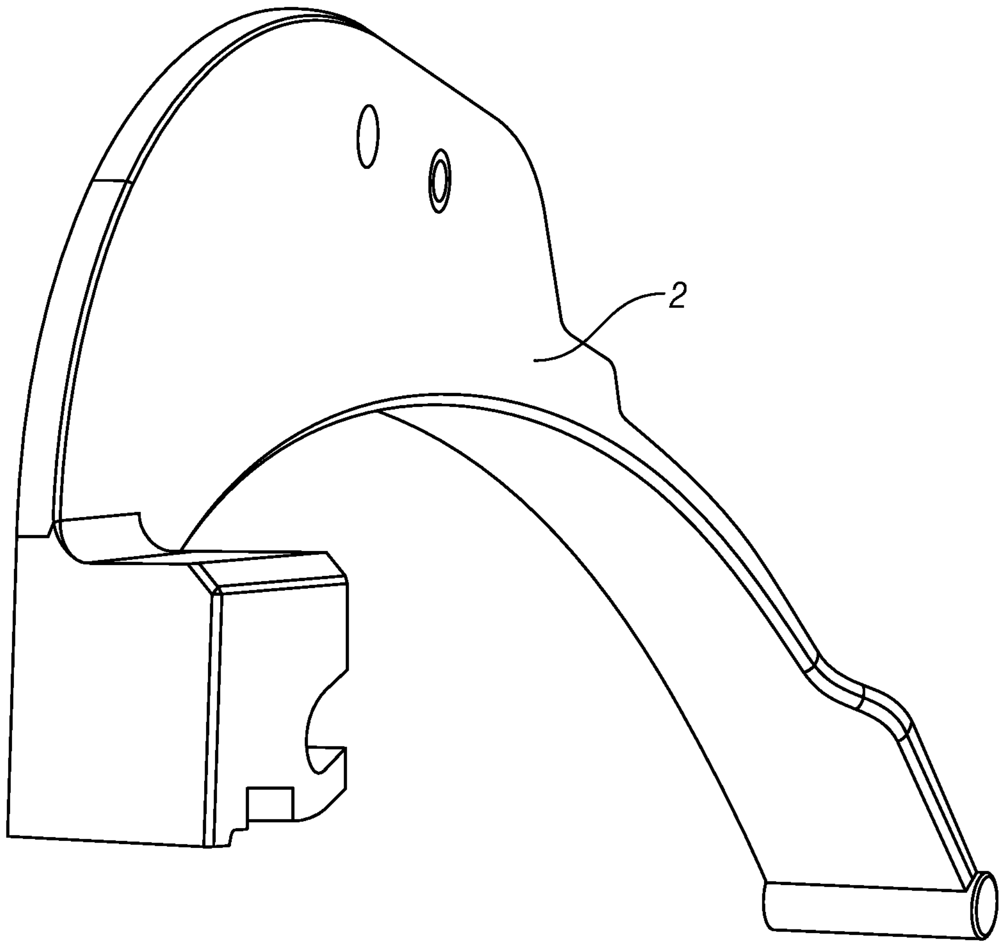
FIG. 10 is a perspective view of the laryngoscope blade of the intubation device of FIG. 1.
Figure 11:
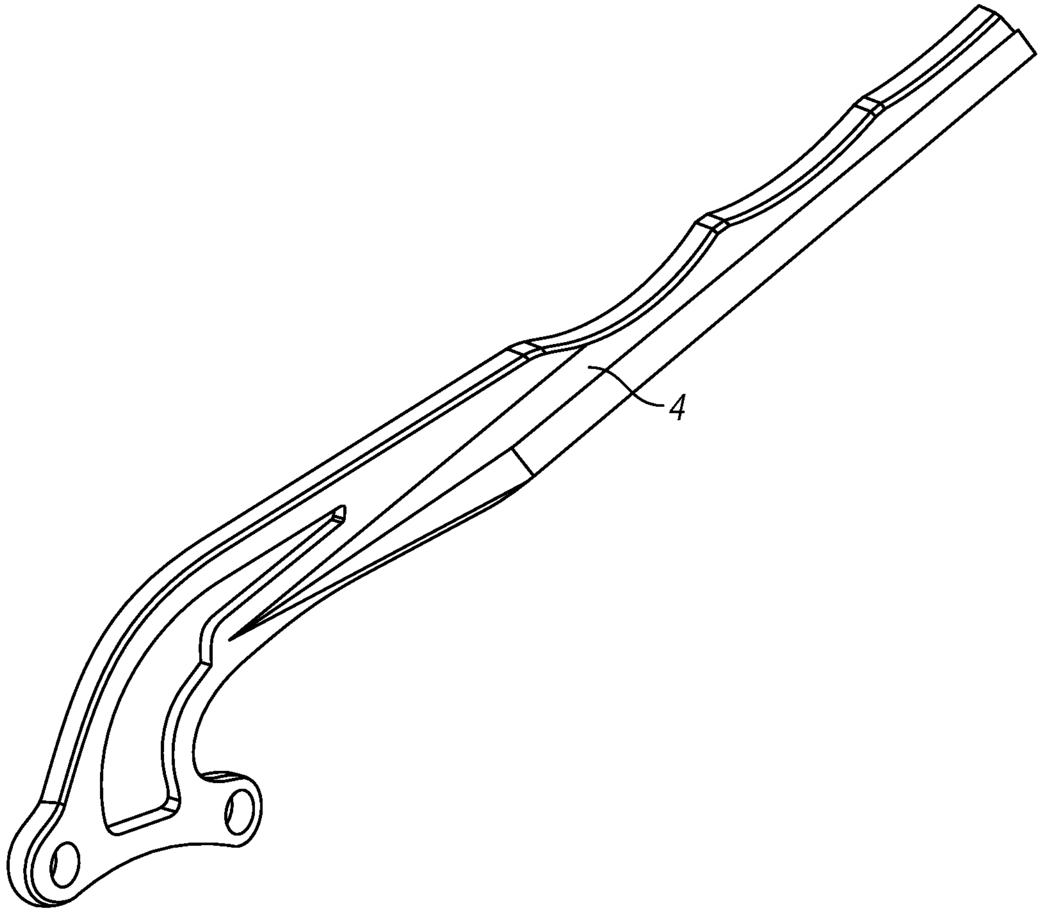
FIG. 11 is a perspective view of the actuating lever of the intubation device of FIG. 1.
Figure 12:
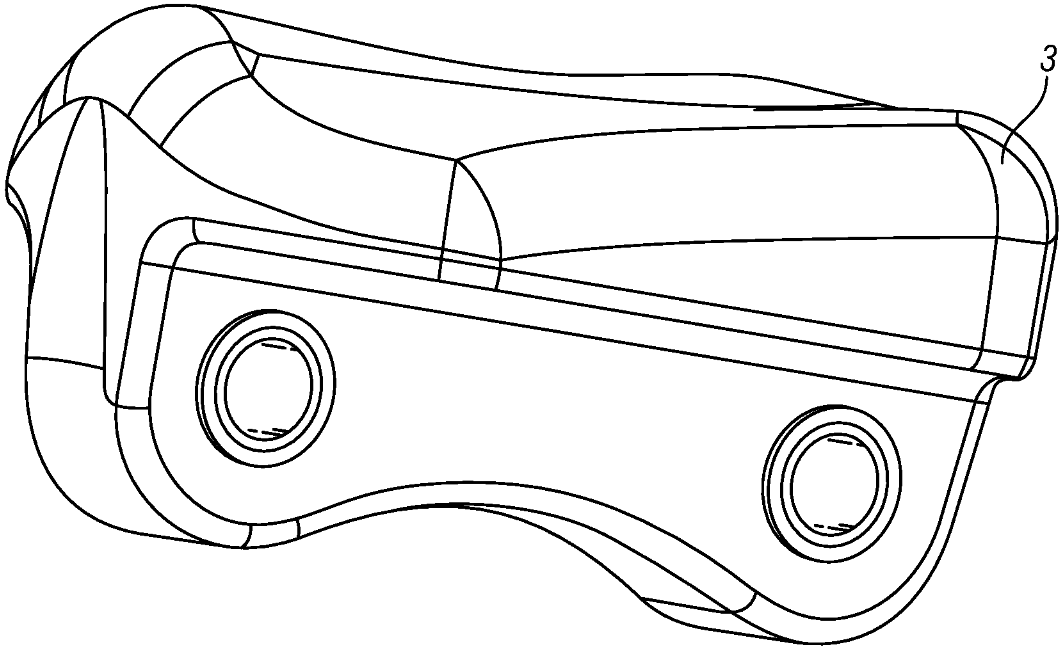
FIG. 12 is a perspective view of the hard palate pivot support of the intubation device of FIG. 1.
Figure 13:
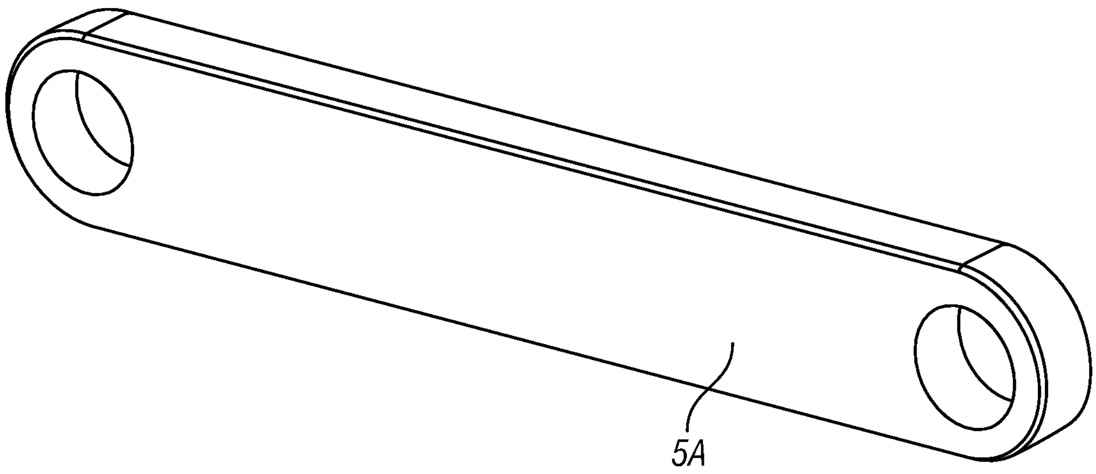
FIG. 13 is a perspective view of a first actuating arm of the intubation device of FIG. 1. Such first actuating arm has two points of connection. It is connected to the actuating lever and a second actuating arm.
Figure 14:
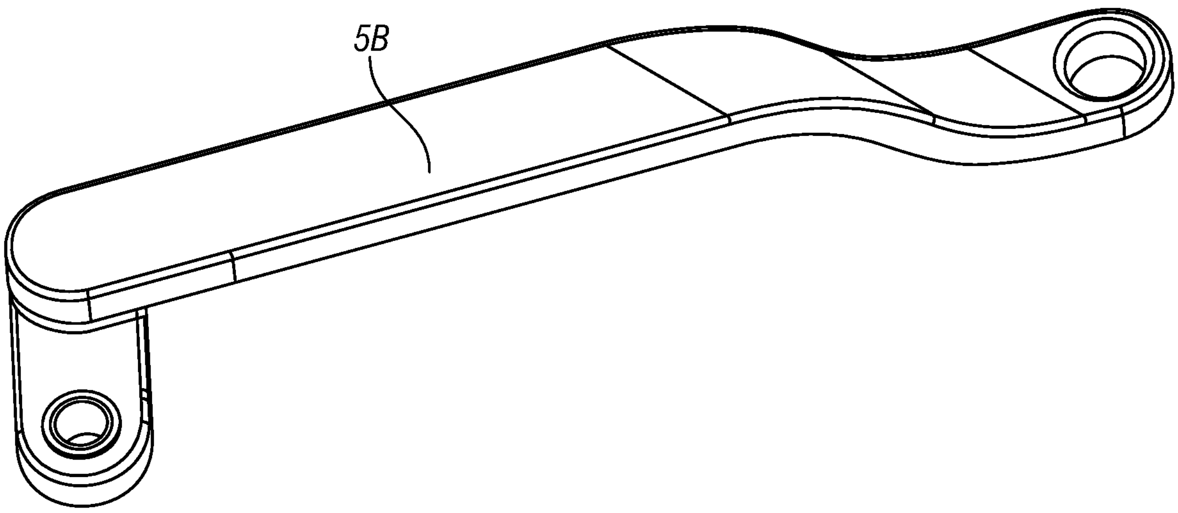
FIG. 14 is a perspective view of the second actuating arm of the intubation device of FIG. 1. Such second actuating arm has three points of connection. It is connected to the first actuating arm. Additionally, such second actuating arm is connected to the laryngoscope blade and the hard palate pivot support.
Figure 15:
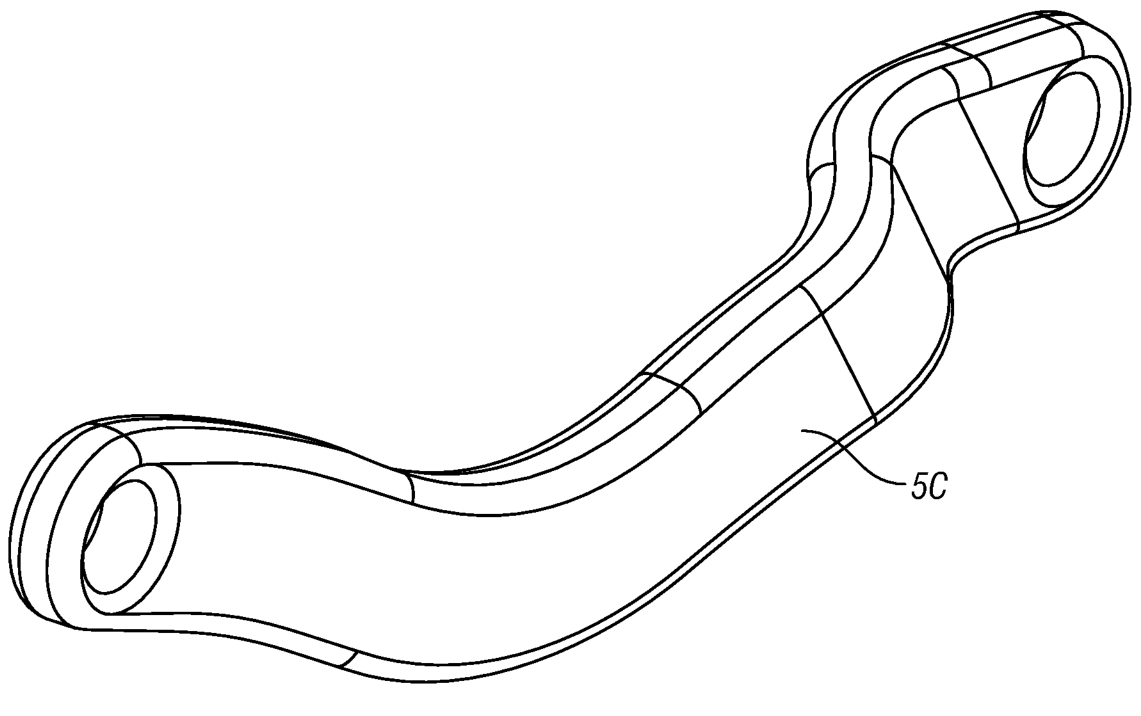
FIG. 15 is a perspective view of the third actuating arm of the intubation device of FIG. 1. Such third actuating arm is connected to the laryngoscope blade and the hard palate pivot support.

Referring to FIGS. 1 to 15, a device for oral intubation is disclosed. In one example embodiment, the device utilizes a laryngoscope blade 2 and hard palate pivot support 3 that is positioned into the airway (or oropharynx) through the opening in the mouth. The device is unlike any other device in that it is utilizes a spring activated lever 4 on the handle 1 that is designed to be easily operated with one hand. In addition to ease of use, the device's design benefits the patient by protecting the patient's teeth, gums, palate and all other soft tissue in the mouth and oropharynx from injury that commonly occurs with the current intubation method. The blade 2 and hard palate pivot support 3 may be collapsed together via the spring (best shown in FIG. 3) for easy insertion; once the device is in the proper position inside a patient's mouth, the lever 4 may be depressed or pulled down spreading the laryngoscope blade 2 and the hard palate pivot support 3 apart at a specific angle and distance from each other. In one embodiment, the device is designed with the proper distance and opening angle to allow for a wide open view of the vocal chords 10 and adequate room for visualization and insertion of a endotracheal tube (best shown in FIGS. 6 to 8).

Figure 1:
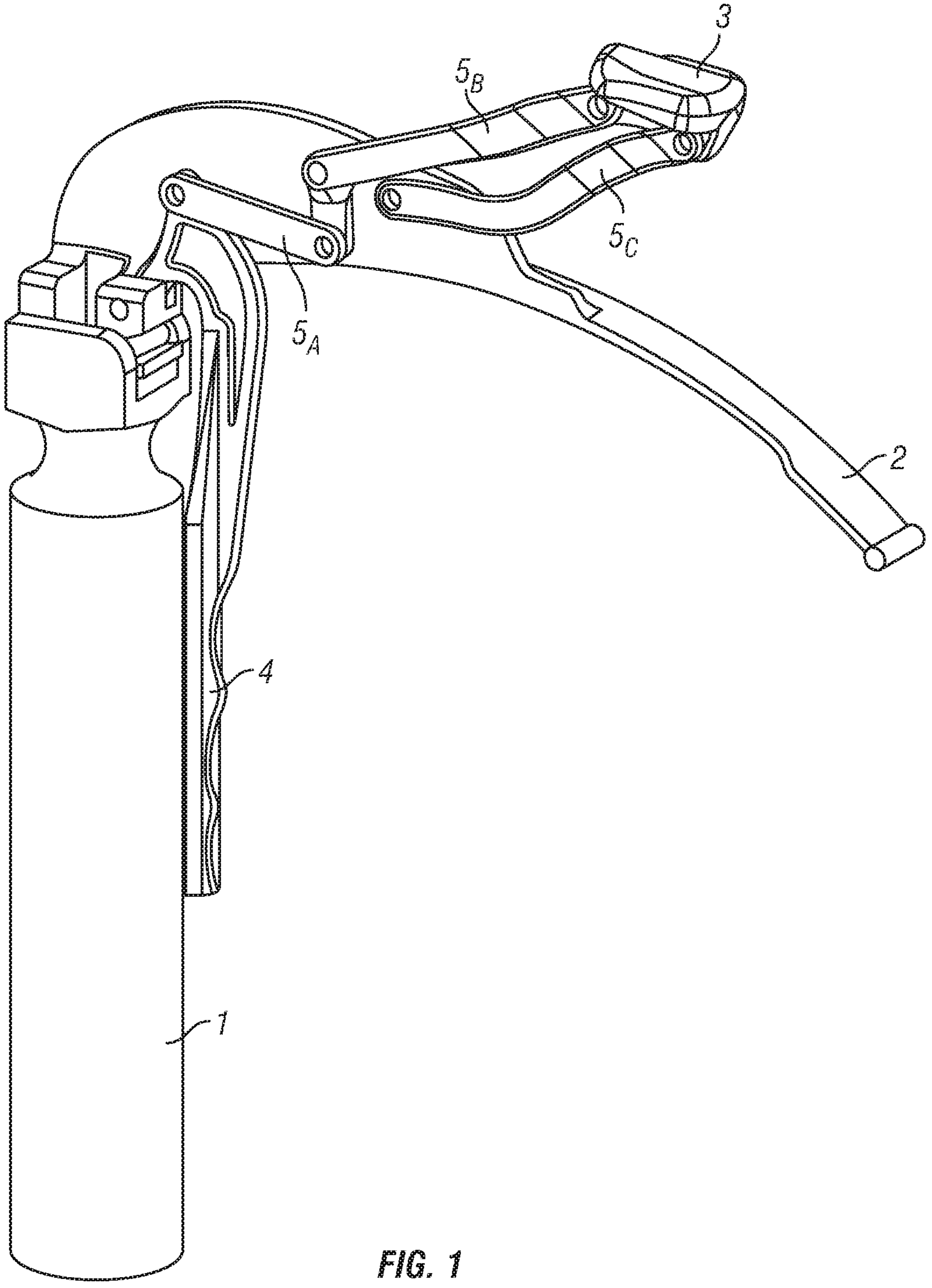
FIG. 1 is a perspective view of the intubation device. In such depiction, the device is in the depressed state as the lever is pulled down.
Figure 2:
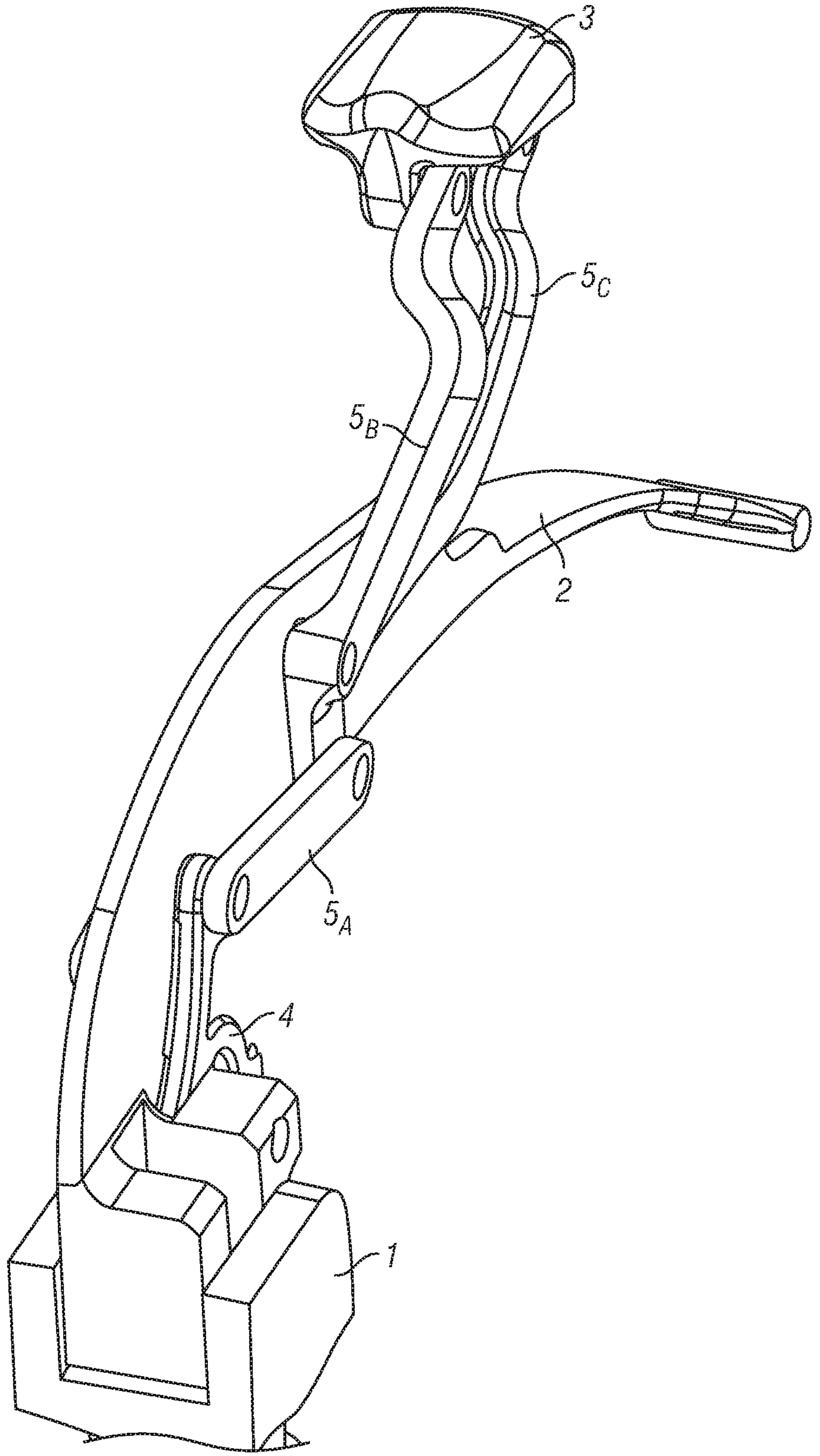
FIG. 2 is a partial back perspective view of the intubation device in FIG. 1.
Figure 3:
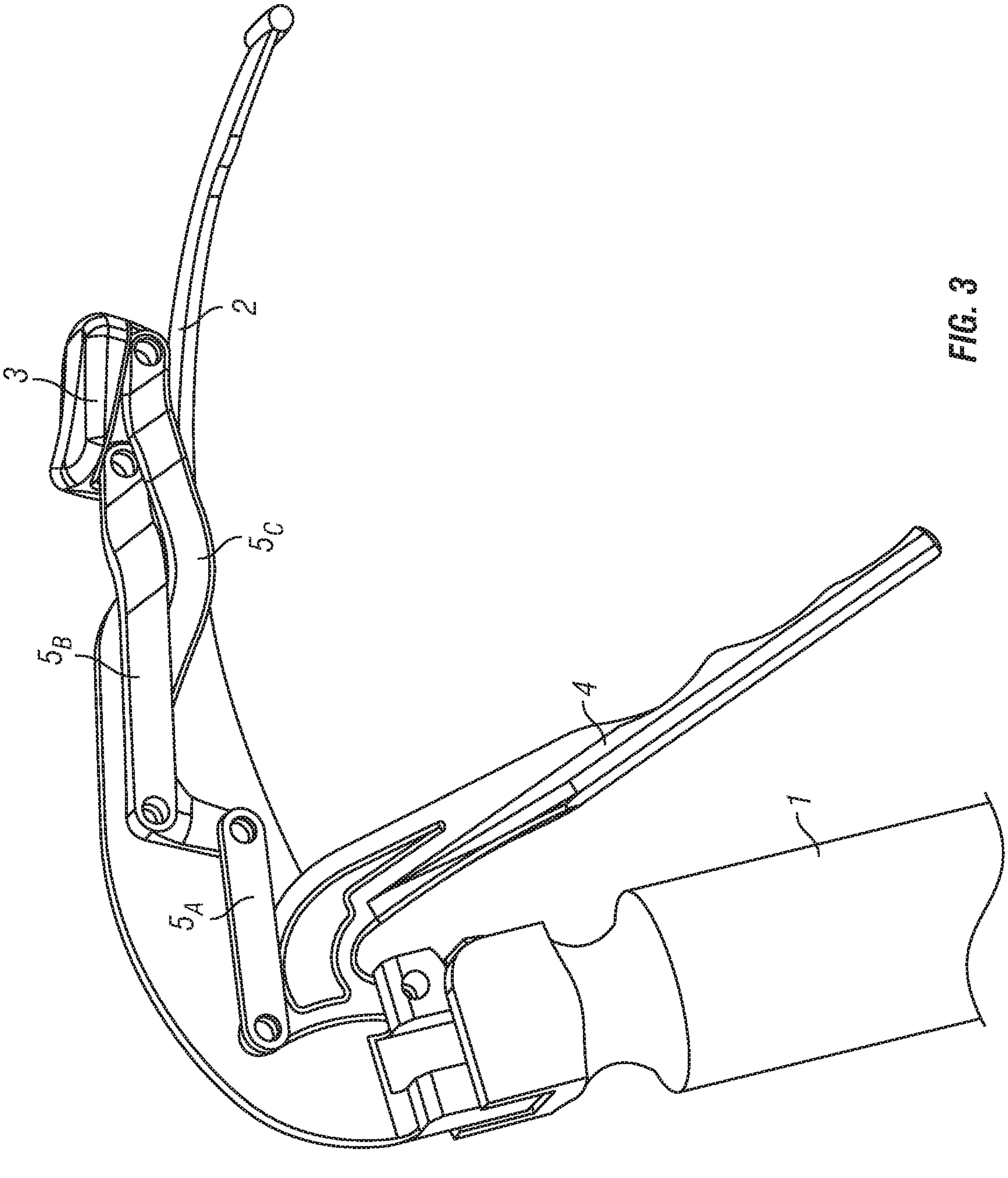
FIG. 3 is a side perspective view of the intubation device. In such depiction, the device is in not in the depressed state as the lever is not depressed or pulled down.
Figure 4:
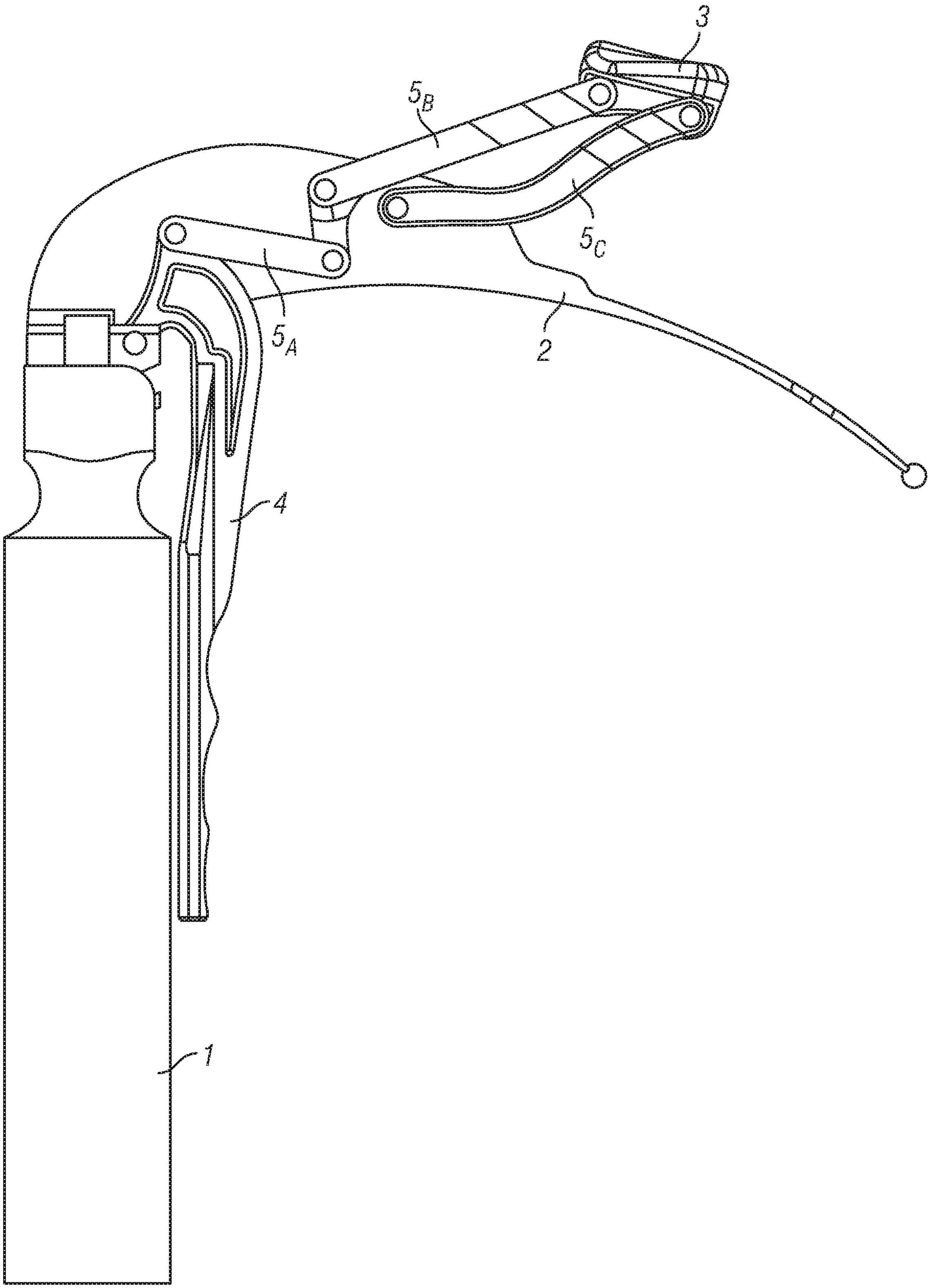
FIG. 4 is a right side perspective view of the intubation device of FIG. 1.
Figure 5:
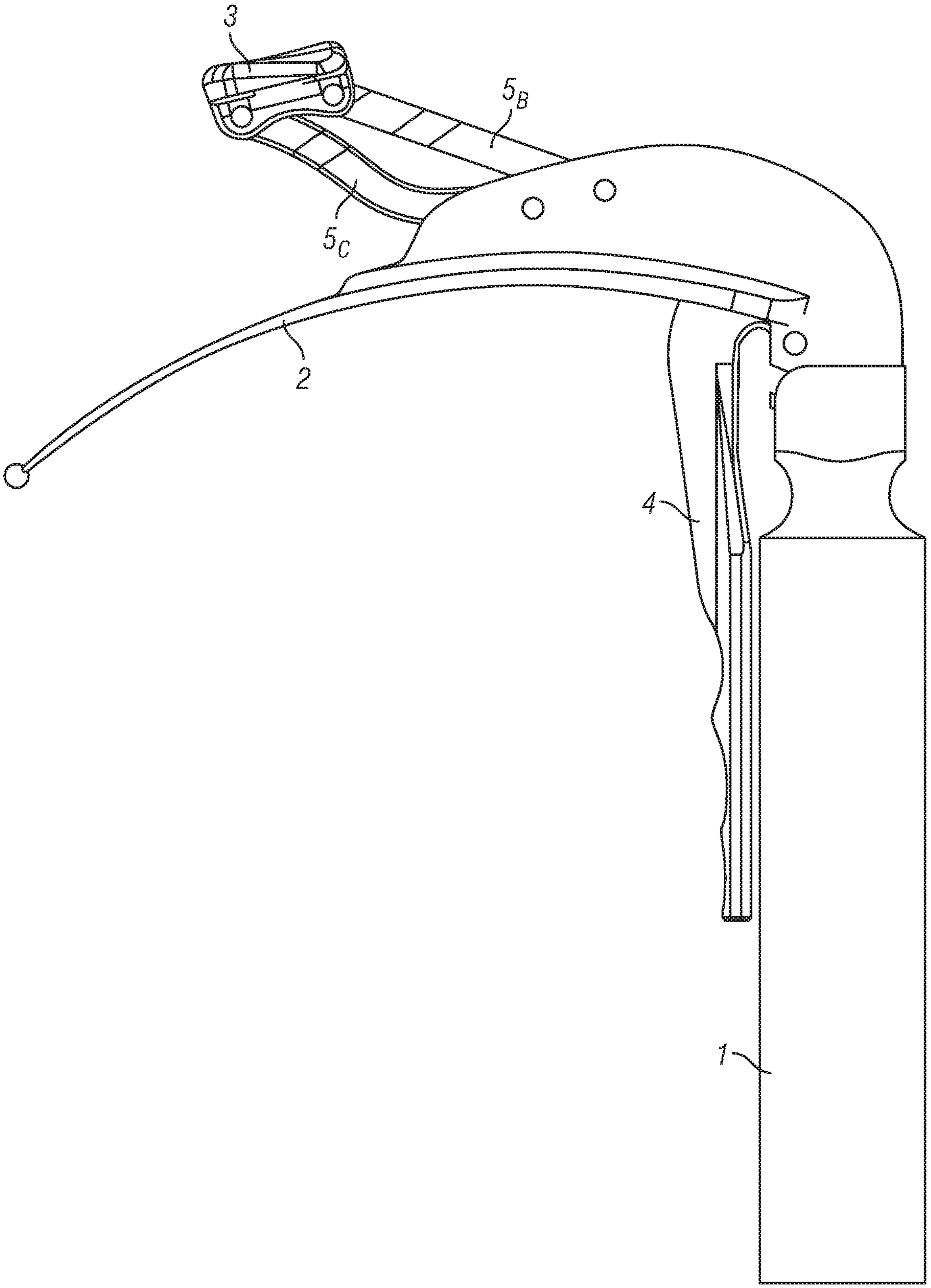
FIG. 5 is a left side perspective view of the intubation device of FIG. 1.

Referring now to FIG. 3, in one example embodiment, the device is collapsed in its resting state (or non depressed state) making insertion of the device easier. Referring now to FIGS. 1-15, the anatomical design is designed to protect the patient from injury. The laryngoscope blade 2 and hard palate pivot support 3 are offset and positioned for optimal utilization meaning it will open and provide the widest view possible of the trachea. The device is designed to release automatically and pressure is easily controlled by the provider. The handle 1 and lever 4 are designed for easy one handed operation requiring minimal physical strength. The hard palate pivot 3 has two apertures (shown in FIG. 12) and is attached to the blade 2 having two apertures (see FIG. 10) with actuating arms 5B and 5C on the side of the blade 2 to allow for direct visualization and easy insertion of an endotracheal tube.

In one example embodiment, laryngoscope blade 2 has a proximal end and a distal end. The proximal end of the blade 2 attached to handle 1. The distal end of blade 2 in inserted into the mouth of a patient. In one example embodiment, the blade 2 has two apertures for attaching to actuating arms 5B and 5C. The size and the length of blade 2 may vary as desired by one of skill in the art. In one example embodiment, laryngoscope blade 2 has a tip on the distal end. Actuating arm 5A has two apertures on each distal end. Arm 5A is connected to lever 4 at one end and actuating arm 5B at the opposite end. Actuating arm 5B is substantially L-shaped and three points of attachment. At each distal end of actuating arm 5B, an aperture exists to allow attachment to the pivot support 3 and the actuating arm 5A. Actuating arm 5B is also attached to blade 2 at the perpendicular junction of actuating arm 5B. Actuating arm 5C has two apertures on each distal end. Arm 5C is connected to blade 2 at one end hard palate pivot support at the opposite end. Actuating arms 5A, 5B and 5C allow movement between the lever 4 and hard palate pivot support 3.

A method of using the device to provide oral intubation to a patient comprises positioning the laryngoscope blade 2 and the hard palate pivot support 3 into the oropharynx through the opening of a patient's mouth. Handle 1 is used to guide the blade 2 into the proper positions. The blade 2 and the hard palate pivot support 3 may be collapsed together to allow them to be inserted between the tongue 16 and the hard palate 14 of the patient 12 (best shown in FIGS. 7 and 8). Once the device is positioned inside the patient's mouth, the actuating lever 4 may be depressed which moves the actuating arms 5A, 5B and 5C, wherein such actuating arms cohesive work together to spread apart the laryngoscope blade 2 and hard palate pivot support 3. This action opens the oropharynx for the necessary view of the vocal chords 10. The endotracheal tube may then be placed through the vocal chords and into the trachea for a successful intubation.

In one embodiment, the device may be made of surgical steel, except for the hard palate pivot support 3, which may be made of a softer synthetic plastic or rubber. The device may be made of other materials as desired by one of skill in the art. Referring to FIGS. 1-15, the hard palate pivot support 3 may be shaped or curved to protect the patient's hard palate 12 from injury. In one example embodiment, the material used may be easily sterilized to allow for multiple uses.

The foregoing disclosure has been set forth merely to illustrate the invention and is not intended to be limiting. Since modifications of the disclosed embodiments incorporating the spirit and substance of the disclosure may occur to persons skilled in the art, the disclosure should be construed to include everything within the scope of the disclosure and equivalents thereof.

I claim:

1. A device used for oral intubation on a patient, the device comprises:

a handle;

a laryngoscope blade having a proximal end and a distal end, wherein the proximal end of the blade is attached to the handle;

a lever attached to the proximal end of the blade, wherein the lever is spring activated; and a hard palate pivot support having a first aperture and a second aperture;

wherein the hard palate pivot support is connected to the laryngoscope blade by a second actuating arm and a third actuating arm, wherein said second actuating arm comprises a third aperture for attaching the second actuating arm to the laryngoscope blade and a fourth aperture for attaching the second actuating arm to the hard palate pivot support, wherein said third actuating arm comprises a fifth aperture for attaching the third actuating arm to the laryngoscope blade and a sixth aperture for attaching the third actuating arm to the hard palate pivot support.

2. A method for providing oral intubation procedure to a patient using the device of claim 1, wherein the method comprises the following steps a. obtaining the oral intubation device disclosed in claim 1;

b. positioning the laryngoscope blade and the hard palate pivot support of the device into the patient's oropharynx through the opening of said patient's mouth;

c. depressing the lever until the laryngoscope blade and the hard palate pivot support open the oropharynx such that the patient's vocal chords are visible; and d. inserting an endotracheal tube through the vocal chords and into the patient's trachea.

3. The device of claim 1, wherein the device is made of surgical steel.

4. The device of claim 1, wherein the hard palate pivot support is made of synthetic plastic or rubber.

5. The device of claim 1, wherein the laryngoscope blade has a tip on the distal end.

* * * * *